United States Patent
Gao et al.

(10) Patent No.: US 11,723,879 B2
(45) Date of Patent: Aug. 15, 2023

(54) LYCOPENE MICRO-CAPSULE POWDER AND PREPARATION METHOD THEREOF

(71) Applicant: Chenguang Biotech Group Co., Ltd., Hebei (CN)

(72) Inventors: Wei Gao, Hebei (CN); Jianzhong Xu, Hebei (CN); Xiangyu Yang, Hebei (CN); Hong Tian, Hebei (CN); Yamei Li, Hebei (CN); Xinchao Jia, Hebei (CN)

(73) Assignee: Chenguang Biotech Group Co., Ltd., Hebei (CN)

( * ) Notice: Subject to any disclaimer, the term of this patent is extended or adjusted under 35 U.S.C. 154(b) by 59 days.

(21) Appl. No.: 16/896,011

(22) Filed: Jun. 8, 2020

(65) Prior Publication Data

US 2020/0297655 A1  Sep. 24, 2020

Related U.S. Application Data

(63) Continuation of application No. PCT/CN2017/115271, filed on Dec. 8, 2017.

(51) Int. Cl.
| A61K 31/01 | (2006.01) |
| A61K 9/16 | (2006.01) |
| A61K 47/22 | (2006.01) |
| A61K 47/36 | (2006.01) |

(52) U.S. Cl.
CPC ............ *A61K 31/01* (2013.01); *A61K 9/1623* (2013.01); *A61K 9/1658* (2013.01); *A61K 47/22* (2013.01); *A61K 47/36* (2013.01)

(58) Field of Classification Search
CPC .... A61K 31/01; A61K 9/1623; A61K 9/1658; A61K 47/22; A61K 47/36
See application file for complete search history.

(56) References Cited

U.S. PATENT DOCUMENTS

2003/0064074 A1  4/2003  Chang et al.

FOREIGN PATENT DOCUMENTS

| CN | 1928098 | 3/2007 |
| CN | 101292965 | 10/2008 |
| CN | 103555802 | 2/2014 |
| CN | 104431690 | 3/2015 |
| CN | 106038511 | 10/2016 |
| CN | 106074462 | 11/2016 |
| CN | 106344510 A | * 1/2017 | ............ A61K 31/01 |
| CN | 105595341 B | * 12/2018 | |
| WO | WO 2019/109346 | 6/2019 |

OTHER PUBLICATIONS

Cheung, I., "Enzymatic production of protein hydrolysates from steelhead (Oncorhynchus mykiss) skin gelatin as inhibitors of dipeptidyl-peptidase IV and angiotensin-I converting enzyme", 2017, Journal of Functional Foods, 28, 254-264 (Year: 2017).*
Suganya, V., Microencapsulation and Nanoencapsulation: A Review, 2017, International Journal of PHarmaceutical and Clinical Research, 9, 3, 233-239 (Year: 2017).*
Belo, I., How is sugar use in the pharmaceutical industry, 2019, Ragus; screenshot from: https://www.ragus.co.uk/how-is-sugar-used-in-the-pharmaceutical-industry/) (Year: 2019).*
Machine translation of CN 1006074462 by Google; Yang, X., et al., 2016 (Year: 2016).*
Machine Translation of CN 105595341 B by Google; Shi, H., et al., 2016 (Year: 2016).*
Zhang, et al., machine translation of CN 106344510 A provided by FIT via PE2E, 2016 (Year: 2016).*

* cited by examiner

*Primary Examiner* — Bethany P Barham
*Assistant Examiner* — Ayaan A Alam
(74) *Attorney, Agent, or Firm* — Levine Bagade Han LLP

(57) ABSTRACT

The present invention discloses a method for preparing a lycopene micro-capsule powder, wherein lycopene is fully mixed with an aqueous phase to obtain a lycopene emulsion, and the emulsion is then ground to a particle size less than 1 μm, and spray dried. The aqueous phase comprises: a gelatin enzymatic hydrolysate with a molecular weight of 5,000-10,000 Da, disaccharide, polysaccharide, and an antioxidant. The disaccharide is one or more of sucrose, maltose and lactose; and the polysaccharide is one or more of pullulan and chitosan.

17 Claims, No Drawings

LYCOPENE MICRO-CAPSULE POWDER AND PREPARATION METHOD THEREOF

CROSS-REFERENCE TO RELATED APPLICATIONS

This application is a continuation International Patent Application Number PCT/CN2017/115271 filed Dec. 8, 2017, the content of which is incorporated herein by reference in its entirety.

TECHNICAL FIELD

The invention relates to a micro-capsule technology of pigment, in particular to a preparation method of lycopene micro-capsule powder.

BACKGROUND

Lycopene is a kind of carotenoids, is one of the strongest antioxidants found in plants in nature, and has important physiological functions. In recent years, epidemiological studies have shown that, compared with other carotenoids, lycopene shows more significant effects in treatment and prevention of a variety of chronic diseases such as tumors, cancers, cardiovascular diseases and arteriosclerosis, and in enhancement of the body immunity. Therefore, the research of lycopene has attracted more and more people's attention.

Lycopene is a non-cyclic planar polyunsaturated aliphatic hydrocarbon containing eleven conjugated double bonds and two non-conjugated double bonds in its chemical structural formula. Lycopene has strong resistance to oxidation, has unstable properties, and is easily oxidized and degraded by the effects of light, heat and oxygen, which greatly limits application scope thereof. Micro-capsule technology can improve the stability of lycopene by effectively reducing the reaction of active substances to external environmental factors such as light, oxygen and water, thereby increasing application of lycopene in functional products. There are many studies on the application of micro-capsule technology of lycopene in functional nutrition. For example, patent application No. CN106038511A proposes a method for preparing nano-sized lycopene micro-encapsulated cold water-dispersed powders, in which a solvent is used to fully dissolve and homogenize lycopene and the compounded nonionic surfactant and the like to obtain nano-sized lycopene micro-capsule powder. The lycopene micro-capsule powder prepared by this method has a poor color, and the use of toxic solvents such as ether, petroleum ether, ethyl acetate, acetone, chloroform, and benzene in the preparation process is likely to cause harm to the human body. Patent application No. CN104431690A provides a lycopene micro-capsule particle and preparation process thereof, in which vegetable oil is used to disperse lycopene crystals to prepare the oil phase, and the product still exhibits the dark red color of lycopene, which is poor in hue.

SUMMARY OF THE INVENTION

The object of the present invention is to overcome the defects in the prior art, and to provide a preparation method of lycopene micro-capsule powder with good hue and stable properties.

Specifically, the method provided by the present invention comprises: fully mixing lycopene with an aqueous phase to obtain a lycopene emulsion; then grinding the emulsion to a particle size of less than 1 μm, and spray drying.

The present invention optimizes specific components in the aqueous phase to ensure that lycopene is encapsulated in the wall material composed of the components, thereby having good comprehensive properties. Specifically, the aqueous phase in the present invention comprises enzymatic hydrolysate of gelatin, a disaccharide, a polysaccharide, and an antioxidant.

Gelatin is a commonly used encapsulating wall material for micro-capsules. Commercially available gelatin generally has a large molecular weight of 15000 to 250,000 Da, and dense spatial network structure. The product obtained after encapsulating has a dark color tone, a brightness difference of color difference of generally less than 20, and a relatively poor grade. In the method provided by the present invention, enzymatic hydrolysis of gelatin could decrease the molecular weight of gelatin, so as to ensure that the product obtained after encapsulating lycopene with the wall material of the gelatin has good color and luster. Specifically, in the present invention, it is preferable that the gelatin in the gelatin enzymatic hydrolysate has a molecular weight of 5000 to 10000 Da.

In a preferred embodiment of the present invention, the gelatin enzymatic hydrolysate may be prepared by a method comprising the following steps: adding gelatin to water, and adding protease under conditions of 55 to 65° C. and pH value of 7.5 to 8.5 for enzymatic hydrolysis, after enzymatic hydrolysis is completed, subjecting the resultant to boiling, and then cooling and keeping the temperature at 55 to 65° C. to obtain the gelatin enzymatic hydrolysate. The protease may be mercapto protease, preferably papain.

In a specific embodiment, it is preferable that the mass ratio of gelatin to water is (1-2):(3-4), and the dosage of the protease is 2.0% to 3.0% of the mass of gelatin.

In the present invention, on the basis of optimizing the gelatin enzymatic hydrolysate, it is preferred that the disaccharide is selected from sucrose, maltose and/or lactose, and the polysaccharide is pullulan polysaccharide and/or chitosan. The use of the above-mentioned preferred sugar components can ensure the synergistic effect thereof with the gelatin enzymatic hydrolysate so as to form a denser network structure for encapsulating lycopene, so that the lycopene micro-capsule powder has good color and luster and stability.

The antioxidant in the present invention is used to prevent lycopene from oxidative inactivation. It is sufficient to use food-grade natural antioxidants commonly used in the art, such as one or a mixture of ascorbic acid and vitamin E.

In order to further improve the above synergistic effect and ensure that the lycopene micro-capsule powder has good color and luster and stability, the amount of each component is optimized in the present invention. As a preferred embodiment of the present invention, the aqueous phase comprises: gelatin enzymatic hydrolysate with a molecular weight 5000 to 10000 Da obtained from 1 to 2 parts of gelatin and 3 to 4 parts of water as raw materials through enzymatic hydrolysis, 2 to 3 parts of disaccharide, 0.3 to 0.5 parts of polysaccharide, and 0.1 to 0.2 parts of antioxidant.

During the preparation process, the aqueous phase can be fully stirred at 55 to 65° C., for example, at a rotation speed of 30 to 50 r/min for 30 to 60 min to ensure that the components are fully mixed to obtain homologous aqueous phase.

In the present invention, the lycopene and the aqueous phase are preferably mixed in a specific ratio, and in terms of the gelatin in the aqueous phase, the mass ratio of the lycopene to gelatin is preferably 1:(1-2). By the above technical solution, it is ensured that the lycopene could be fully and evenly embedded, and the lycopene and the micro-capsule wall in the obtained micro-capsule powder have an appropriate size ratio, so that the micro-capsule powder has good color and luster and stability.

In the present invention, the lycopene and the aqueous phase are fully mixed, preferably sheared and stirred at 7000 to 9000 r/min at 55 to 65° C. to obtain a lycopene emulsion with an excellent mixing degree. In order to ensure the quality of the obtained product, the raw material of lycopene used is preferably lycopene crystals.

It is further preferred that the grinding comprises grinding to a particle size of 200 to 600 nm in order to obtain a product with good performance and using effect. The grinding can be carried out by a nano-grinder to obtain a desired particle size. For example, the grinding is carried out at a rotation speed of 1600 to 1800 r/min for 1.0 to 2.0 h.

In the present invention, the spray drying is carried out by conventional spray drying methods in the art. As a preferred embodiment of the present invention, the following parameters may be used: an inlet air temperature of 165 to 180° C., an outlet air temperature of 90 to 105° C., and an air rate of 300 to 500 mL/h.

As a preferred embodiment of the present invention, the method for preparing the lycopene micro-capsule powder comprises the following specific steps:

(1) adding 1 to 2 parts of gelatin to 3 to 4 parts of water, adding protease for enzymatic hydrolysis, boiling, and then cooling to obtain gelatin enzymatic hydrolysate with a molecular weight of 5000 to 10000 Da at a temperature of 55 to 65° C.;

(2) adding 2 to 3 parts of disaccharide, 0.3 to 0.5 parts of polysaccharide and 0.1 to 0.2 parts of antioxidant to the gelatin enzymatic hydrolysate, stirring and dissolving sufficiently to obtain an aqueous phase;

(3) adding 1 part of lycopene to the aqueous phase, shearing and stirring at 7000 to 9000 r/min at 55 to 65° C. to obtain a lycopene emulsion;

(4) grinding the lycopene emulsion to a particle size of 200 to 600 nm to obtain a lycopene microemulsion;

(5) spray drying the lycopene microemulsion to obtain lycopene micro-capsule powder.

The invention also claims the lycopene micro-capsule powder prepared by the above-mentioned method. The color values of the lycopene micro-capsule powder provided by the present invention could be: L*38.5 to 40.5; a*29.0 to 30.0; b*19.0 to 20.0. After long-term storage, the lycopene content and color values remain stable.

In the method provided by the present invention, a lycopene micro-capsule powder is obtained by using enzymatically-hydrolyzed gelatin as a wall material, combining the grinding effect of a nano-grinder, and using spray drying, which solves the problems of dark color luster and poor stability to light, heat and free radical. Compared with the dark red color of lycopene crystals and ordinary lycopene powder, the color tone of the obtained lycopene micro-capsule powder is cherry red, which is brighter and more vivid, and could improve the appetite of consumers. Moreover, the obtained lycopene micro-capsule powder has high stability to light, heat and free radicals. There is no obvious change in color after being kept at room temperature for one year, and the content retention rate could reach 97% or more. The method provided by the invention is simple, environmentally friendly, low in production cost, and suitable for large-scale preparation of lycopene micro-capsule powder.

DETAILED DESCRIPTION OF THE INVENTION

The specific embodiments of the present invention will be further described in detail in combination with Examples.

The following Examples are intended to illustrate the present invention, but not intended to limit to the scope of the present invention.

Example 1

The present Example provides a preparation method of lycopene micro-capsule powder, specifically comprising the following steps:

(1) 150 g of gelatin was added to 225 g of purified water, and papain was added in an amount of 3.75 g. The resulting solution was adjusted to a pH of 7.5, and subjected to enzymatic hydrolysis at a temperature of 55° C. in water bath for 3 h. The resultant was boiled for 15 min, and then cooled to 55° C. to obtain a gelatin enzymatic hydrolysate. The gelatin in the gelatin enzymatic hydrolysate had a molecular weight of 7000 Da;

(2) 225 g of sucrose, 22.5 g of pullulan polysaccharide, 10 g of ascorbic acid, and 5 g of vitamin E were added to the gelatin enzymatic hydrolysate, and the resultant was stirred at 65° C. at a rotation speed of 40 r/min for 45 min to obtain an aqueous phase;

(3) 75 g of lycopene crystals with a content of 90 wt % was added to the aqueous phase while stirring, and the resultant was sheared at a shear speed of 9000 r/min and a temperature of 65° C. for 10 min to obtain a lycopene emulsion;

(4) The lycopene emulsion was ground by a nano-grinder at a rotation speed of 1700 r/min for 1.5 h to obtain a lycopene microemulsion with a particle size of 400 nm;

(5) The lycopene microemulsion was spray-dried with an inlet air temperature of 175° C., an outlet air temperature of 100° C., and a flow rate of 500 mL/h to obtain a lycopene micro-capsule powder.

Example 2

The present Example provides a preparation method of lycopene micro-capsule powder, specifically comprising the following steps:

(1) 200 g of gelatin was added to 437.5 g of purified water, and papain was added in an amount of 6 g. The resulting solution was adjusted to a pH of 8.0, and subjected to enzymatic hydrolysis at a temperature of 60° C. in water bath for 5 h. The resultant was boiled for 15 min, and then cooled to 60° C. to obtain a gelatin enzymatic hydrolysate. The gelatin in the gelatin enzymatic hydrolysate had a molecular weight of 8000 Da;

(2) 250 g of maltose, 62.5 g of pullulan polysaccharide, 2.5 g of ascorbic acid and 10 g of vitamin E were added to the gelatin enzymatic hydrolysate, and the resultant was stirred at 60° C. at a rotation speed of 30 r/min for 50 min to obtain an aqueous phase;

(3) 125 g of lycopene crystals with a content of 90 wt % was added to the aqueous phase while stirring, and the resultant was sheared at a shear speed of 8000 r/min and a temperature of 60° C. for 15 min to obtain a lycopene emulsion;

(4) The lycopene emulsion was ground by a nano-grinder at a rotation speed of 1800 r/min for 1 h to obtain a lycopene microemulsion with a particle size of 500 nm;

(5) The lycopene microemulsion was spray-dried with an inlet air temperature of 180° C., an outlet air temperature of 105° C., and a flow rate of 400 mL/h to obtain a lycopene micro-capsule powder.

Example 3

The present Example provides a preparation method of lycopene micro-capsule powder, specifically comprising the following steps:

(1) 165 g of gelatin was added to 440 g of purified water, and papain was added in an amount of 3.3 g. The resulting solution was adjusted to a pH of 8.5, and subjected to enzymatic hydrolysis at a temperature of 65° C. in water bath for 4 h. The resultant was boiled for 15 min, and then cooled to 65° C. to obtain a gelatin enzymatic hydrolysate. The gelatin in the gelatin enzymatic hydrolysate had a molecular weight of 5000 Da;

(2) 275 g of lactose, 44 g of chitosan and 22 g of ascorbic acid were added to the gelatin enzymatic hydrolysate, and the resultant was stirred at 65° C. at a rotation speed of 50 r/min for 30 min to obtain an aqueous phase;

(3) 110 g of lycopene crystals with a content of 90 wt % was added to the aqueous phase while stirring, and the resultant was sheared at a shear speed of 7000 r/min and a temperature of 65° C. for 20 min to obtain a lycopene emulsion;

(4) The lycopene emulsion was ground by a nano-grinder at a rotation speed of 1800 r/min for 2.0 h to obtain a lycopene microemulsion with a particle size of 200 nm;

(5) The lycopene microemulsion was spray-dried with an inlet air temperature of 170° C., an outlet air temperature of 95° C., and a flow rate of 300 mL/h to obtain a lycopene micro-capsule powder.

Example 4

The present Example provides a preparation method of lycopene micro-capsule powder, specifically comprising the following steps:

(1) 100 g of gelatin was added to 320 g of purified water, and papain was added in an amount of 2.5 g. The resulting solution was adjusted to a pH of 8.2, and subjected to enzymatic hydrolysis at a temperature of 60° C. in water bath for 3.5 h. The resultant was boiled for 15 min, and then cooled to 55° C. to obtain a gelatin enzymatic hydrolysate. The gelatin in the gelatin enzymatic hydrolysate had a molecular weight of 10000 Da;

(2) 125 g of sucrose, 125 g of maltose, 20 g of pullulan polysaccharide, 15 g of chitosan, and 15 g of vitamin E were added to the gelatin enzymatic hydrolysate, and the resultant was stirred at 55° C. at a rotation speed of 45 r/min for 60 min to obtain an aqueous phase;

(3) 100 g of lycopene crystals with a content of 92 wt % was added to the aqueous phase while stirring, and the resultant was sheared at a shear speed of 7500 r/min and a temperature of 55° C. for 30 min to obtain a lycopene emulsion;

(4) The lycopene emulsion was ground by a nano-grinder at a rotation speed of 1600 r/min for 1.0 h to obtain a lycopene microemulsion with a particle size of 600 nm;

(5) The lycopene microemulsion was spray-dried with an inlet air temperature of 165° C., an outlet air temperature of 90° C., and a flow rate of 450 mL/h to obtain a lycopene micro-capsule powder.

Comparative Example 1

(1) 150 g of gelatin was added to 225 g of purified water, the resultant was boiled for 15 min, and then cooled to 55° C. to obtain a solution. The gelatin in the gelatin solution had a molecular weight of 45000 Da;

(2) 225 g of sucrose, 22.5 g of pullulan polysaccharide, 10 g of ascorbic acid and 5 g of vitamin E were added to the gelatin solution, and the resultant was stirred at 65° C. at a rotation speed of 40 r/min for 45 min to obtain an aqueous phase;

(3) 75 g of lycopene crystals with a content of 90 wt % was added to the aqueous phase while stirring, and the resultant was sheared at a shear speed of 9000 r/min and a temperature of 65° C. for 10 min to obtain a lycopene emulsion;

(4) The lycopene emulsion was ground by a nano-grinder at a rotation speed of 1700 r/min for 1.5 h to obtain a lycopene microemulsion with a particle size of 1.2 μm;

(5) The lycopene microemulsion was spray-dried with an inlet air temperature of 175° C., an outlet air temperature of 100° C., and a flow rate of 500 mL/h to obtain a lycopene micro-capsule powder.

Experimental Example 1: Chroma Comparison

Three kinds of lycopene micro-capsule powder were randomly purchased from the market, and the chroma thereof was tested together with the lycopene provided in Examples 1 to 4. The test results were shown in Table 1.

TABLE 1

| Test value of chroma of lycopene micro-capsule powder | | | |
|---|---|---|---|
| | L* | a* | b* |
| Example 1 | 38.5 | 30.0 | 19.5 |
| Example 2 | 40.2 | 29.0 | 20.0 |
| Example 3 | 39.0 | 29.6 | 19.3 |
| Example 4 | 39.4 | 29.3 | 19.7 |
| Comparative Example 1 | 57.2 | 13.09 | 1.32 |
| commercially available product 1 | 23.72 | 8.44 | 4.64 |
| commercially available product 2 | 27.99 | 9.52 | 4.39 |
| commercially available product 3 | 32.13 | 7.89 | 5.07 |

It can be seen from the results in Table 1 that, the method provided by the present invention can effectively improve the color tone of the obtained product compared with the dark red color of other products, making it brighter and more vivid.

Experimental Example 2: Stability Test

The lycopene micro-capsule powders provided in Examples 1 to 4 were kept at a temperature of 25° C. and a humidity of 60% in dark for one year. The content of lycopene and chroma were tested. The test results were shown in Table 2.

TABLE 2

| | Direct test without storage | | | | Test after keeping for one year | | | |
|---|---|---|---|---|---|---|---|---|
| | content of lycopene (wt %) | L* | a* | b* | content of lycopene (wt %) | L* | a* | b* |
| Example 1 | 10.94 | 38.5 | 30.0 | 19.5 | 10.75 | 39.6 | 29.4 | 19.9 |
| Example 2 | 11.54 | 40.2 | 29.0 | 20.0 | 11.40 | 41.04 | 27.9 | 20.6 |
| Example 3 | 11.50 | 39.0 | 29.6 | 19.3 | 11.27 | 40.3 | 28.6 | 19.7 |
| Example 4 | 10.68 | 39.4 | 29.3 | 19.7 | 10.44 | 40.0 | 28.9 | 19.0 |
| Comparative Example 1 | 10.90 | 57.2 | 13.09 | 1.32 | 6.65 | 57.9 | 4.8 | −0.87 |

Changes in content of lycopene and chroma value

It can be seen from the results in Table 2 that the lycopene micro-capsule powder provided by the present invention has good stability, and there is no obvious change in the content of lycopene and chroma value after storage for one year.

The above contents are only preferred embodiments of the present invention and are not intended to limit the present invention. Any modification, equivalent replacement, improvement and the like made according to the spirit and principle of the present invention shall be regarded as within the protection scope of the invention.

We claim:

1. A method for preparing lycopene micro-capsule powder, comprising:
   adding 1 to 2 parts of gelatin to 3 to 4 parts of water, adding protease for enzymatic hydrolysis, and boiling, and then cooling to obtain gelatin enzymatic hydrolysate with a molecular weight of 5000 to 10000 Da at a temperature of 55 to 65° C.;
   adding 2 to 3 parts of disaccharide, 0.3 to 0.5 parts of polysaccharide and 0.1 to 0.2 parts of antioxidant to the gelatin enzymatic hydrolysate, stirring and dissolving sufficiently at 40 to 50 r/min to obtain an aqueous phase;
   adding 1 part of lycopene to the aqueous phase, shearing and stirring at 7000 to 9000 r/min at 55 to 65° C. for 10 to 20 minutes to obtain a lycopene emulsion, wherein the lycopene comprises a content of 90 wt % to 92 wt %;
   grinding the lycopene emulsion to a particle size of less than 1 μm to obtain a lycopene microemulsion; and
   spray drying the lycopene microemulsion to obtain lycopene micro-capsule powder.

2. The method according to claim 1, wherein the gelatin enzymatic hydrolysate is prepared by a method comprising the following steps: adding gelatin to water, and adding protease under conditions of 55 to 65° C. and pH value of 7.5 to 8.5 for enzymatic hydrolysis, after enzymatic hydrolysis is completed, subjecting the resultant to boiling, and then cooling and keeping at the temperature of 55 to 65° C. to obtain the gelatin enzymatic hydrolysate;
   the protease is papain, and/or the dosage of the protease is 2.0% to 3.0% of the mass of gelatin.

3. The method according to claim 1, wherein the disaccharide is one or more selected from sucrose, maltose and lactose;
   and/or, the polysaccharide is one or more selected from pullulan polysaccharide and chitosan;
   and/or, the antioxidant is one or more selected from ascorbic acid and vitamin E.

4. The method according claim 1, wherein the mass ratio of the lycopene to gelatin contained in the aqueous phase is 1:(1-2).

5. The method according to claim 1, wherein the grinding comprises grinding to a particle size of 200 to 600 nm;
   the grinding is carried out by a nano-grinder at a rotation speed of 1600 to 1800 r/min for 1.0 to 2.0 h.

6. The method according to claim 1, wherein the conditions for spray drying comprises: an inlet air temperature of 165 to 180° C., an outlet air temperature of 90 to 105° C., and an air rate of 300 to 500 mL/h.

7. A lycopene micro-capsule powder prepared by the method according to claim 1.

8. The method according to claim 1, wherein the gelatin enzymatic hydrolysate is prepared by a method comprising the following steps: adding gelatin to water, and adding protease under conditions of 55 to 65° C. and pH value of 7.5 to 8.5 for enzymatic hydrolysis, after enzymatic hydrolysis is completed, subjecting the resultant to boiling, and then cooling and keeping at the temperature of 55 to 65° C. to obtain the gelatin enzymatic hydrolysate.

9. The method according to claim 1, wherein the disaccharide is one or more selected from sucrose, maltose and lactose;
   and/or, the polysaccharide is one or more selected from pullulan polysaccharide and chitosan;
   and/or, the antioxidant is one or more selected from ascorbic acid and vitamin E.

10. The method according to claim 2, wherein the disaccharide is one or more selected from sucrose, maltose and lactose;
    and/or, the polysaccharide is one or more selected from pullulan polysaccharide and chitosan;
    and/or, the antioxidant is one or more selected from ascorbic acid and vitamin E.

11. The method according claim 2, wherein the mass ratio of the lycopene to gelatin contained in the aqueous phase is 1:(1-2).

12. The method according to claim 3, wherein the mass ratio of the lycopene to gelatin contained in the aqueous phase is 1:(1-2).

13. A lycopene micro-capsule powder prepared by the method according to claim 2.

14. A lycopene micro-capsule powder prepared by the method according to claim 3.

15. A lycopene micro-capsule powder prepared by the method according to claim 4.

16. A lycopene micro-capsule powder prepared by the method according to claim 5.

17. A lycopene micro-capsule powder prepared by the method according to claim 6.

* * * * *